(12) United States Patent
Haggis et al.

(10) Patent No.: US 11,464,452 B2
(45) Date of Patent: Oct. 11, 2022

(54) SYSTEM AND METHOD FOR ATTACHING AND SECURING A SENSOR

(71) Applicant: Life Detection Technologies, Inc., Sunnyvale, CA (US)

(72) Inventors: John Haggis, San Jose, CA (US); Eric Howie, Henderson, NV (US); Mark Flowers, Los Gatos, CA (US)

(73) Assignee: Life Detection Technologies, Inc., Sunnyvale, CA (US)

( * ) Notice: Subject to any disclaimer, the term of this patent is extended or adjusted under 35 U.S.C. 154(b) by 309 days.

(21) Appl. No.: 16/890,970

(22) Filed: Jun. 2, 2020

(65) Prior Publication Data

US 2020/0375542 A1    Dec. 3, 2020

Related U.S. Application Data

(60) Provisional application No. 62/856,564, filed on Jun. 3, 2019.

(51) Int. Cl.
*A61B 5/00* (2006.01)
*A61B 5/11* (2006.01)
*A47C 21/00* (2006.01)
*A61B 5/024* (2006.01)
*A61B 5/08* (2006.01)

(52) U.S. Cl.
CPC ............ *A61B 5/6892* (2013.01); *A47C 21/00* (2013.01); *A61B 5/02444* (2013.01); *A61B 5/0823* (2013.01); *A61B 5/1115* (2013.01)

(58) Field of Classification Search
CPC ... A47C 21/00; A61B 5/6892; A61B 5/02444; A61B 5/02427; A61B 5/0823; A61B 5/1115
USPC ............................................................ 5/658
See application file for complete search history.

(56) References Cited

U.S. PATENT DOCUMENTS

| 5,724,990 | A   | * | 3/1998  | Ogino     | A61B 5/6892 |
|           |     |   |         |           | 600/587     |
| 5,902,255 | A   | * | 5/1999  | Ogino     | A61B 5/6887 |
|           |     |   |         |           | 600/595     |
| 6,297,738 | B1  | * | 10/2001 | Newham    | G08B 21/22  |
|           |     |   |         |           | 340/568.1   |
| 6,778,090 | B2  | * | 8/2004  | Newham    | A61B 5/1115 |
|           |     |   |         |           | 340/562     |
| 7,331,071 | B1  | * | 2/2008  | Cherubini | A47C 31/00  |
|           |     |   |         |           | 5/652       |
| 7,652,581 | B2  | * | 1/2010  | Gentry    | G08B 21/0461|
|           |     |   |         |           | 340/573.1   |

(Continued)

FOREIGN PATENT DOCUMENTS

| EP | 2702973 A1 | * | 3/2014 | ........... A61B 5/1036 |
| WO | WO-2005079530 A2 | * | 9/2005 | ............... A61B 5/11 |
| WO | WO-2019060250 A1 | * | 3/2019 | ............... A61B 5/11 |

OTHER PUBLICATIONS

Sleepace, "Sleep Tracking Pad Model: P300," downloaded Sep. 1, 2020, http://www.sleepace.com/tracking_pad.html (5 pages).

(Continued)

*Primary Examiner* — Robert G Santos
(74) *Attorney, Agent, or Firm* — Fiala & Weaver P.L.L.C.

(57) ABSTRACT

A sensor strap system according to an embodiment of the present disclosure includes: a sensor capable of detecting physical or physiological activities or conditions of a target subject; a top strap extending along a top surface of a bed, the top strap configured to secure the sensor to the top surface of the bed; and a circumferential strap extending about a circumference of the bed and coupled with the top strap.

20 Claims, 3 Drawing Sheets

(56) References Cited

U.S. PATENT DOCUMENTS

| | | | | |
|---|---|---|---|---|
| 7,836,529 | B2* | 11/2010 | Cherubini | G08B 21/22 |
| | | | | 5/652 |
| 8,672,842 | B2* | 3/2014 | Kenalty | A61B 6/0407 |
| | | | | 600/587 |
| 2002/0070866 | A1* | 6/2002 | Newham | A61B 5/1115 |
| | | | | 340/666 |
| 2005/0190068 | A1* | 9/2005 | Gentry | A61B 5/11 |
| | | | | 340/665 |
| 2008/0136226 | A1* | 6/2008 | Cherubini | A47C 31/00 |
| | | | | 297/217.2 |
| 2011/0001622 | A1* | 1/2011 | Gentry | G08B 21/0461 |
| | | | | 340/573.1 |
| 2011/0308015 | A1* | 12/2011 | Newham | G08B 21/22 |
| | | | | 5/499 |
| 2012/0053424 | A1* | 3/2012 | Kenalty | A61B 5/6892 |
| | | | | 600/300 |
| 2014/0059778 | A1* | 3/2014 | Jalbert | A61G 7/057 |
| | | | | 5/690 |
| 2020/0214621 | A1* | 7/2020 | Keroles | A61B 5/6831 |
| 2020/0375542 | A1* | 12/2020 | Haggis | A47C 21/00 |

OTHER PUBLICATIONS

Mdrebel, "Bed Bridge Kit Twin to King Converter Kit—Memory Foam Filler Pad and Connector Strap," downloaded Sep. 1, 2020, https://www.amazon.com/dp/B07SX2H1TZ/ref=sspa_dk_detail_5?psc=1&pd_rd_i=B07SX2H1TZ&pd_rd_w=WFeQf&pf_rd_p=48d372c1-f7e1-4b8b-9d02-4bd86f5158c5&pd_rd_wg=JeYe1&pf_rd_r=9XQ5ZJYRJPA5QWCJG59A&pd_rd_r=040d324b-7ea5-40ef-97b9-e541992b87e4&spLa=ZW5jcnlwdGVkUXVhbGlmaWVyPUExODFQQIJFTTRBUjgmZWSjcnlwdGVkSWQ9QTA4NzYyMTUyMVZOUEhVRkVDRFFQyJmVuY3J5cHRlZEFkSWQ9QTAwNzMwMDMxMDFRTUNDVEdFWUIZJndpZGdldE5hbWU9c3BfZGV0YWlsJmFjdGlvbj1jbGlja1JZGlyZWN0JmRvTm90TG9nQ2xpY2s9dHJ1ZQ== (8 pages).

Humble Innovations, "Bed Bridge Twin to King Converter Kit—Twin XL and Twin Bed Connector King Maker—2 Unique Adjustable Straps—Memory Foam Slide Reducing Compact Bed Gap Filler—Fits," downloaded Sep. 1, 2020, https://www.amazon.com/humble-Innovations-Bridge-Twin-Converter/dp/B07KRWG5GW (8 pages).

Wet-Stop, "Features of the Wet-Detective Bed Pad Alarm System," downloaded Sep. 1, 2020, https://wetstop.com/features-wet-detective-bed-wetting/ (3 pages).

Sunbeam, "Foot Cuddler Queen/King Heated Mattress Pad," downloaded Sep. 1, 2020, https://www.amazon.com/Sunbeam-Cuddler-Queen-Heated-Mattress/dp/B002M76U76/ref=sr_1_22?dchild=1&keywords=sunbeam+foot+warming+mattress+pad&qid=1590783507&sr=8-22 (7 pages).

\* cited by examiner

SYSTEM AND METHOD FOR ATTACHING AND SECURING A SENSOR

CROSS-REFERENCE TO RELATED APPLICATIONS

This application claims the benefit of and priority to U.S. Provisional Application No. 62/856,564, filed on Jun. 3, 2019, which is incorporated by reference herein in its entirety for all purposes.

BACKGROUND OF THE INVENTION

Many known monitoring systems for beds rely on a type of sensor that works at a distance through the mattress. These are placed below the mattress, against the base of the bed or between the mattress and box springs.

The present invention concerns a monitor for subjects in beds, in chairs, in cribs, and in any other furniture or conveyance or structure which contacts or is in proximity with the subject's back, side, front, or any other suitable external surfaces. Furthermore, this invention requires the sensor be located close to the subject being monitored, for example, between the subject and the mattress or cushion of the furniture.

In some embodiments, in the case of a bed, it is desirable to easily locate the sensor on the top surface of the mattress, to fix it in place regardless of the movement of the mattress or bed coverings, and to allow bed coverings to be applied to the mattress with minimal restriction.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

DETAILED DESCRIPTION

Figure 1:
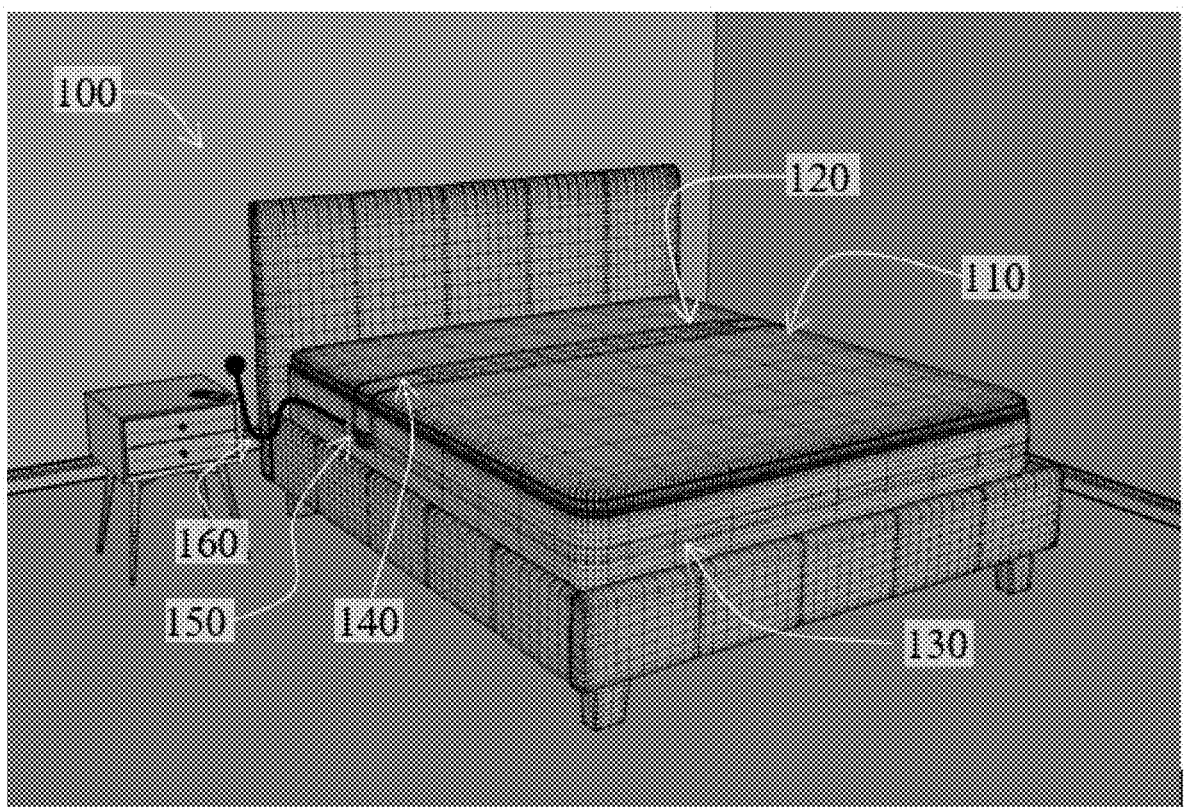
FIG. 1 is an overview diagram of the sensor and strap system attached to a bed mattress according to certain embodiments of the present disclosure.

In the following description, numerous specific details are set forth regarding the systems, methods and media of the disclosed subject matter and the environment in which such systems, methods and media may operate, etc., in order to provide a thorough understanding of the disclosed subject matter. It will be apparent to one skilled in the art, however, that the disclosed subject matter may be practiced without such specific details, and that certain features, which are well known in the art, are not described in detail in order to avoid complication of the disclosed subject matter. In addition, it will be understood that the examples provided below are exemplary, and that it is contemplated that there are other systems, methods and media that are within the scope of the disclosed subject matter.

The invention includes sensor strap systems and methods for attaching and securing a sensor strap system to an object (e.g., a mattress, cushion, chair, conveyance, or other type of furniture) ("Base"). According to some embodiments, a sensor of the sensor strap system is placed/positioned to contact or juxtaposition with a sensor target (such as a human or animal subject). According to some embodiments, the sensor strap system is configured to be secured to a Base effortlessly, with minimum interference with the accessories of the Base (such as sheet cover and mattress padding etc.). According to some embodiments, the sensor strap system facilitates detection of physical and/or physiological activities/conditions of a target subject. The activities and conditions include, for example, the target subject's general movement (e.g., getting into or out of the chair or mattress), and/or the target subject's physiological state such as heart and lung activity or coughing patterns etc. During the detection, the target subject may be reclined or otherwise in contact with the sensor of the sensor strap system (e.g., sensor pad, plate, sheet, or any other suitable components of the sensor strap system). In some embodiments, the sensor of the sensor strap system is a sensor pad. In some embodiments, the sensor pad is rigid. In some embodiments, the sensor pad is flexible. In some embodiments, the sensor pad is positioned to physically contact a subject (e.g., human or animal subject).

According to certain embodiments, the sensor of the sensor strap system (e.g., sensor pad or sensor plate) is secured to a body-contacting surface of an object (such as top of a mattress, or the sitting surface of a chair). However, the invention is applicable to any object with a broad surface, and enough compression resistance to allow a circumferential strap to secure the sensor strap system, without causing substantial deformation to the object.

According to some embodiments, the sensor strap system has means for securing itself to a bed and means for keeping the sensor (e.g., sensor pad) flat over the top surface of the bed. In some embodiments, the means for securing the system include a set of straps configured to keep the sensor pad secured on the mattress. In some embodiments, the set of straps are configured to be easily installed and removed. In some embodiments, the sensor strap system is designed to allow easy exchange of covers, such as bed sheets, so that the covers can be replaced without disrupting sensor pad's position.

According to some embodiments, the sensor strap system has two sets of straps. The first set of straps (e.g., circumferential strap or straps) is designed to run around the circumference of a mattress. In some embodiments, the circumferential strap or straps incorporate various securing mechanisms such as buckles or other suitable tensioning mechanisms designed to help fixing the sensor strap system against the surfaces of the mattress (without the need to run straps underneath the mattress). The second set of straps (e.g., top strap or straps), according to certain embodiments, emerge from the sensor pad and are configured to connect to the circumferential strap or straps. In some embodiments, the top strap or straps extend to the sides of the mattress and connect with the circumferential strap or straps. In some embodiments, the connections of the top strap or straps to the circumferential straps may be permanent. In some embodiments, the connections are accomplished via detachable mechanisms such as clasps, buckles, or any other suitable mechanisms.

In some embodiments, the circumferential strap or straps are made of inelastic materials such as nylon webbing. Circumferential strap or straps made with inelastic material may be coupled with certain tension adjustment mechanisms to allow the strap or straps to take up slack and make the hold more secure. In some embodiments, the circumferential strap or straps are made of an elastic material that may not need tension adjustment mechanisms or buckles to keep the sensor strap system secured. In some embodiments, the circumferential strap or straps incorporate a rigid corner piece to provide a point of reference at one corner of the mattress or other base platform.

In some embodiments, the top strap or straps are made of an elastic material so that when a subject (e.g., human or animal) moves on the top of the bed, the strap or straps could flex to allow for normal elastic depression or extension. According to certain embodiments, the top strap or straps are attached to the circumferential strap or straps with permanent attachments such as stitching or permanent adhesives. In other embodiments, the top strap or straps are connected to circumferential straps via one or more adjustable mechanisms such as buckles. In some embodiments, the attachment mechanisms may be permanent such that the position of the sensor relative to the length of the bed is fixed. In other embodiments, the sensor strap system is configured to allow the sensor pad to connect/attach to different positions along the circumferential strap or straps. Such configuration allows users to adjust the position of the sensor pad along the bed.

According to some embodiments, the sensor pad has electrical connections with one or more electrical conductors. These conductors may be attached to or embedded in the elastic top straps so that they can be routed to the circumferential strap or straps. In some embodiments, the conductors are made of flexible materials that can expand and contract as the top strap or straps flex. In some embodiments, the conductors may extend due to a subject depressing the top of the mattress. In one embodiment, the extension and contraction of the conductors are accomplished via a pattern (e.g., a zig-zag patter or any other suitable patterns) of a flexible cable. In other embodiments, the conductors may be a cable (electric cable) with a slack loop which would allow the cable to extend and retract. In other embodiments, the conductors may be incorporated into the strap or straps by means of conductive threads.

In some embodiments, once the electrical cable reaches the circumferential strap or straps, it travels along the strap or straps to an electronics module. In one embodiment, this module is attached to the circumferential strap or straps. In some embodiments, this module is attached to the top strap or straps as it travels down the side of the mattress (against one side of the mattress). In yet another embodiment the module is free-hanging.

In some embodiments, a secondary cable is used to extend from the module to power supply or other electronics. In some embodiments, the cable travels in the top strap or straps. In some embodiments, the cable passes through a part of the circumferential strap or straps. In some embodiments, the electronic cable is free-hanging in whole or in part.

The invention will be better understood and objects other than those set forth above will become apparent when consideration is given to the following detailed description thereof. Such description makes reference to the annexed drawings disclosed herein.

FIG. 1 illustrates a sensor strap system 100 install on a mattress according to certain embodiments. Sensor strap system 100 has a sensor pad 120 secured to the top of mattress 110. Sensor strap system 100 applies to a mattress 110 as the background or platform. As shown in FIG. 1, the circumferential strap 130 of sensor strap system 100 is secured to the side of mattress 110 without passing anything underneath mattress 110. Further, the top strap 140 of sensor strap system 100 extends over the sides of mattress 110 and connects the circumferential strap 130. On the side of sensor strap system 100, an electronics module 150 is attached to the top strap 140 and connected to its external power or communication cable 160. According to some embodiments, when no subject (e.g., human body) is exerting force on the sensor pad 120, the top strap 140 has minimally-loaded elasticity that keeps the sensor pad 120 flat and in its nominal position to accomplish its sensing function. The top strap 140 also keeps the sensor pad 120 from folding or lifting to disturb the aesthetics of flat sheets or blankets. In some embodiments, the sensor strap system 100 may include more than one circumferential strap and/or more than one top strap. In some embodiments, sensor strap system 100 may include fewer components. In some embodiments, sensor strap system 100 may include suitable additional or alternative components.

Figure 2:
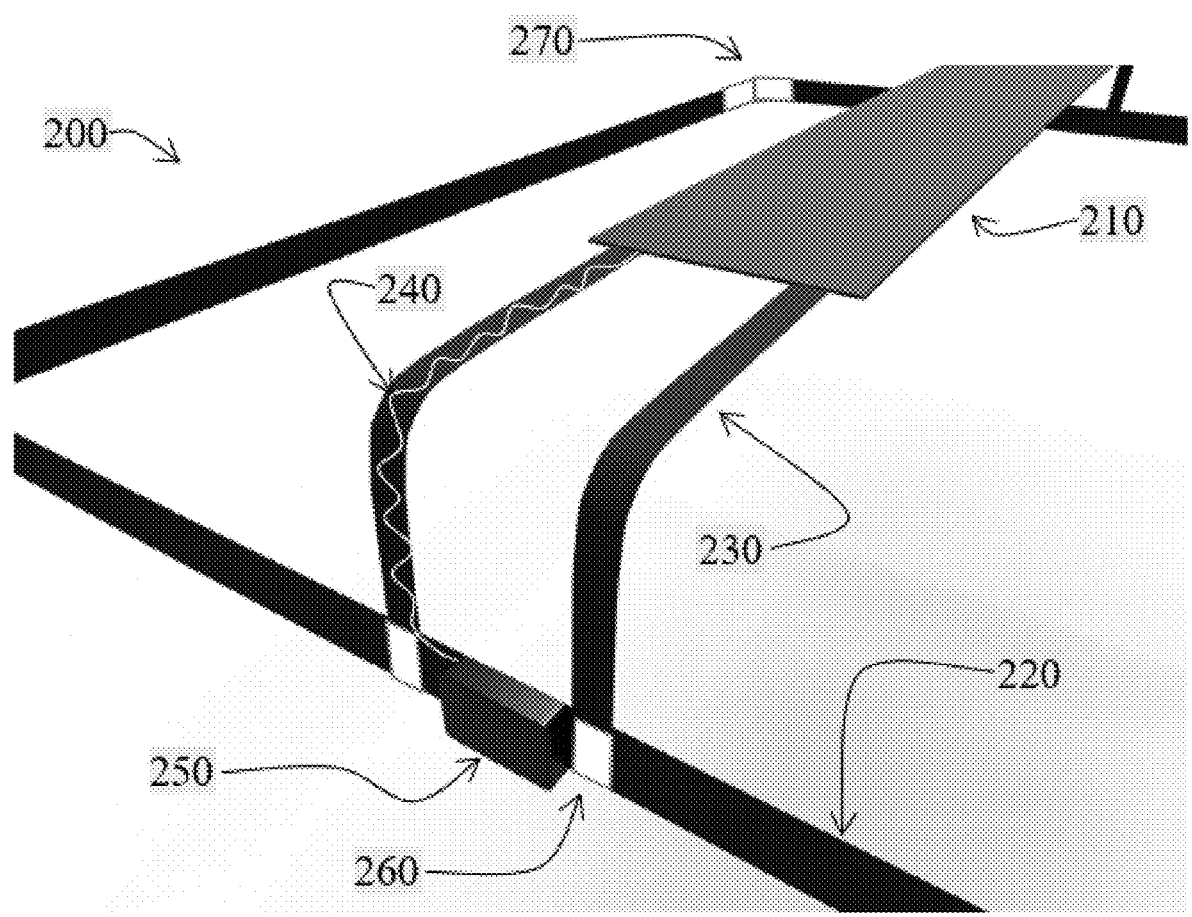
FIG. 2 is a diagram depicting the sensor, the top straps, and the circumferential straps and their attachments according to certain embodiments of the present disclosure.

FIG. 2 illustrates a system 200 for securing a sensor pad to the top of a mattress according to certain embodiments. As shown, system 200 has a sensor pad 210 secured to the circumferential strap 220. In this embodiment, the sensor pad 210 is connected to the circumferential strap 220 via elastic top strap 230 which emerges from permanent attachments to the sensor pad 210 and extends over the edge of the mattress surface to connect to the circumferential strap 220. In some embodiments, the top strap 230 is attached to the circumferential strap 220 by permanent mechanisms such as stitching, adhesive, or any other suitable mechanisms. In some embodiments, the top strap 230 is attached to the circumferential strap 220 by a removable/detachable mechanism such as a buckle or clasp 260. In some embodiments, the buckle or clasp 260 can be any other suitable mechanisms. This buckle or clasp may take up slack in the top straps 230 to ensure that the top strap 230 is taut and minimally stretched when there is no load (e.g., body) on the bed. In some embodiments, the location of the buckle or clasp 260 can change along the circumferential strap 220 to facilitate changing the location of the sensor pad 210 on the top of the mattress. In some embodiments, a rigid corner piece 270 is incorporated to establish a reference point in one or more corners of the mattress. According to some embodiments, the rigid corner piece 270 facilitates positioning of the sensor pad 210. In some embodiments, the electrical cable 240 travels on or within the top strap 230 to connect to an electronics module 250. FIG. 2 depicts electronics module 250 connected to the circumferential strap 220 between clasps 260. In some embodiments, electronics module 250 may be placed at another segment of the circumferential strap 220. In some embodiments, system 200 may include fewer components. In some embodiments, the sensor strap system 200 may include more than one circumferential strap and/or more than one top strap. In some embodiments, system 200 may include suitable additional or alternative components.

Figure 3:
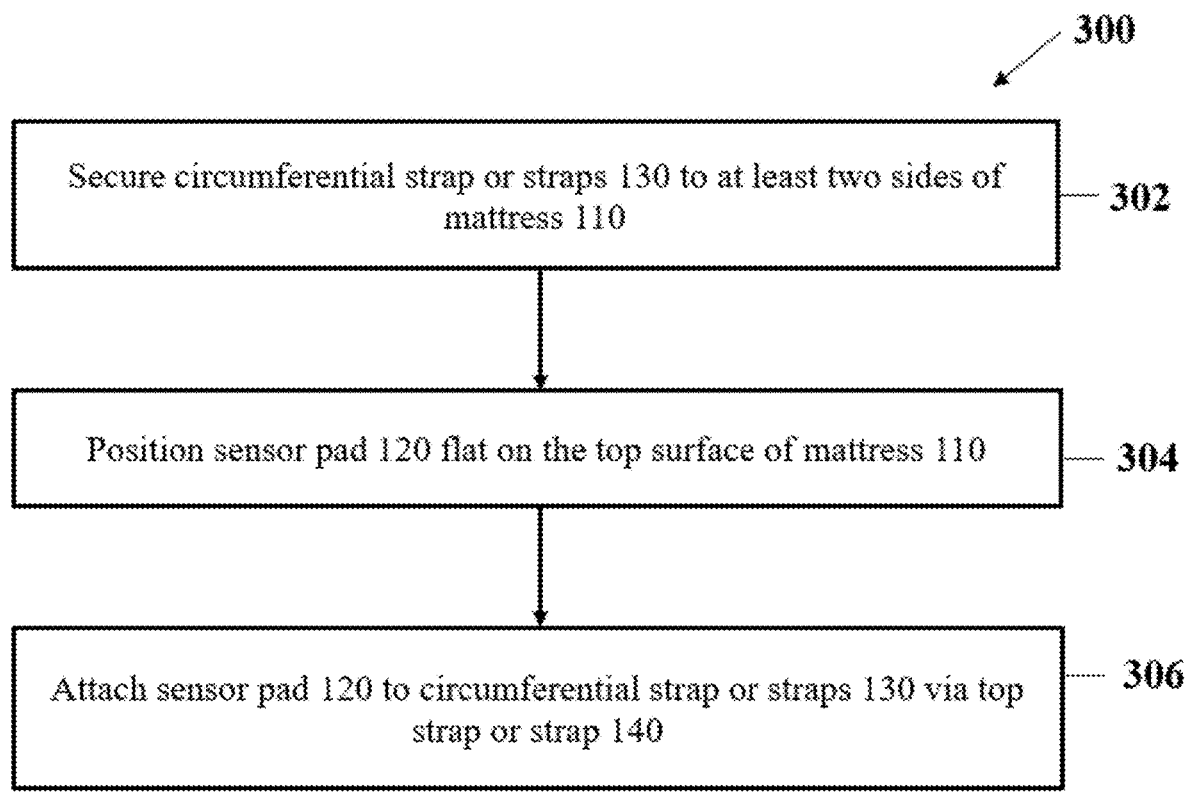
FIG. 3 illustrates a process for attaching and securing a sensor strap system according to certain embodiments of the present disclosure.

FIG. 3 is a flow chart illustrating a process 300 of securing a sensor strap system to a mattress according to certain embodiments of the present disclosure. The process 300 is illustrated in connection with the system 100 shown in FIG. 1 as a non-limiting example. In some embodiments, the process 300 can be modified by, for example, having steps rearranged, changed, added, and/or removed.

At step 302, circumferential strap or straps 130 are secured around the circumference along the sides of mattress 110. In some embodiments, circumferential strap or straps 130 are made of an elastic material. In some embodiments, circumferential strap or straps 130 are made of inelastic materials. In some embodiments, an electronic module is placed on circumferential strap or straps 130. In some embodiments, circumferential strap or straps 130 are connected to top strap or straps 140 via detachable mechanisms such as buckles or clasps. The process 300 then proceeds to step 304.

At step 304, sensor pad 120 is placed flat on mattress 110. In some embodiments, the desired area of detection is adjacent to, or proximate to, the torso of a body that is going to be monitored. In some embodiments, sensor pad 120 is generally placed across the upper-middle section of mattress 110. The process 300 then proceeds to step 306.

At step 306, sensor pad 120 is attached to circumferential strap or straps 130 via top strap or straps 140 that emerge from sensor pad 120. In some embodiments, top strap or straps 140 are made of an elastic material. In some embodiments, top strap or straps 140 are made of inelastic materials. In some embodiments, the top strap or straps 140 have embedded wires/cables that runs to an electronic module located on circumferential strap or straps 130.

It is to be understood that the disclosed subject matter is not limited in its application to the details of construction and to the arrangements of the components set forth in the description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, systems, methods and media for carrying out the several purposes of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

What is claimed is:

1. A sensor strap system for attaching a sensor to a bed, comprising:
   a sensor capable of detecting physical or physiological activities or conditions of a target subject;
   a top strap extending along a top surface of the bed, the top strap configured to secure the sensor to the top surface of the bed; and
   a circumferential strap extending about a circumference of the bed and coupled with the top strap.

2. The sensor strap system of claim 1, wherein the circumferential strap has at least one non-elastic portion to which the top strap is coupled, and at least one elastic portion.

3. The sensor strap system of claim 1, wherein the top strap is coupled with the circumferential strap via a connection mechanism.

4. The sensor strap system of claim 1, wherein the top strap is capable of coupling with the circumferential strap at different positions along the circumferential strap.

5. The sensor strap system of claim 2, wherein an end of the top strap is coupled with the circumferential strap at a fixed position along the circumferential strap to fix a position of the sensor relative to the length of the bed.

6. The sensor strap system of claim 1, wherein the circumferential strap is adjustable.

7. The sensor strap system of claim 5, wherein the circumferential strap further comprises a corner indicator positioned at a corner of the bed.

8. The sensor strap system of claim 7, wherein the corner indicator is a rigid corner piece.

9. The sensor strap system of claim 8, wherein the non-elastic portion of the circumferential strap extends from the corner indicator to the fixed position where the top strap is coupled with the circumferential strap.

10. The sensor strap system of claim 1, wherein the bed comprises a mattress, and wherein the circumferential strap extends about a circumference of the mattress.

11. The sensor strap system of claim 1, further comprising an electronics module coupled with sensor.

12. The sensor strap system of claim 11, wherein the electronics module is attached to the circumferential strap.

13. The sensor strap system of claim 11, wherein the electronics module is attached to the top strap.

14. A sensor strap system for attaching a sensor to a mattress having an outer circumference and corners, comprising:
   a sensor capable of detecting physical or physiological activities or conditions of a target subject;
   a top strap extending along a top surface of the mattress, the top strap configured to secure the sensor to the top surface of the mattress;
   a circumferential strap extending about a circumference of the mattress, the circumferential strap having at least one non-stretchable portion with which the top strap is coupled, and at least one stretchable portion, and further comprising two corner indicators each positioned at one of the corners of the mattress; and
   an electrical conductor connected to the sensor, the electrical conductor arranged along the top strap.

15. The sensor strap system of claim 14, wherein an overall length of the electrical conductor is capable of expanding and contracting while remaining arranged along the top strap to accommodate stretching and contracting of an overall length of the top strap.

16. The sensor strap system of claim 15, wherein the electrical conductor is an electric cable arranged in a zig-zag pattern.

17. The sensor strap system of claim 15, wherein the electrical conductor is an electric cable with a slack loop.

18. A sensor strap system for attaching a sensor pad to a mattress having an outer circumference and four corners, comprising:
   a sensor pad capable of detecting physical or physiological activities or conditions of a target subject;
   a circumferential strap extending about a circumference of the mattress, the circumferential strap having at least one non-elastic portion and at least one elastic portion, the circumferential strap further comprising two corner indicators, each corner indicator positioned at one of the four corners of the mattress; and
   two top straps extending along the top surface of the mattress connecting the sensor pad to the circumferential strap, wherein an end of each of the two top straps is coupled with the circumferential strap at a fixed position along the circumferential strap to fix a position of the sensor relative to the length of the bed;
   wherein the at least one non-elastic portion of the circumferential strap extends along a portion of the length of the mattress from at least one of the two corner indicators to the fixed positions along the circumferential strap where the end of each of the two top straps is coupled with the circumferential strap.

19. The sensor strap system of claim 18, further comprising:
   an electronics module coupled with the sensor pad; and
   an electric cable coupling the electronics module with the sensor pad, the electric cable arranged in a zig-zag pattern along one of the two top straps.

20. The sensor strap system of claim 19, the one of the two top straps having a stretchable overall length such that the zig-zag pattern of the electric cable accommodates stretching of the stretchable overall length.

\* \* \* \* \*